(12) United States Patent
Agahari

(10) Patent No.: US 12,168,127 B2
(45) Date of Patent: Dec. 17, 2024

(54) ANKLE CUFF FOR MANAGING INCONTINENCE

(71) Applicant: Nicky Agahari, Hornsby (AU)

(72) Inventor: Nicky Agahari, Hornsby (AU)

(*) Notice: Subject to any disclaimer, the term of this patent is extended or adjusted under 35 U.S.C. 154(b) by 854 days.

(21) Appl. No.: 17/258,284

(22) PCT Filed: Jul. 5, 2019

(86) PCT No.: PCT/AU2019/050711
§ 371 (c)(1),
(2) Date: Jan. 6, 2021

(87) PCT Pub. No.: WO2020/006607
PCT Pub. Date: Jan. 9, 2020

(65) Prior Publication Data
US 2021/0268278 A1 Sep. 2, 2021

(30) Foreign Application Priority Data

Jul. 6, 2018 (AU) .............................. 2018902463

(51) Int. Cl.
*A61N 1/36* (2006.01)
*A61N 1/05* (2006.01)
*A61M 37/00* (2006.01)

(52) U.S. Cl.
CPC ....... *A61N 1/36007* (2013.01); *A61N 1/0502* (2013.01); *A61N 1/36017* (2013.01);
(Continued)

(58) Field of Classification Search
CPC .............. A61N 1/36007; A61N 1/0502; A61N 1/36017; A61N 1/36031; A61N 1/36034
See application file for complete search history.

(56) References Cited

U.S. PATENT DOCUMENTS 10,729,341 B1* 8/2020 Nyabero ................. A61B 5/05
2006/0206162 A1* 9/2006 Wahlstrand .......... A61N 1/0502
607/46
(Continued)

FOREIGN PATENT DOCUMENTS

WO 2011053607 A1 5/2011
WO 2013036599 A1 3/2013
(Continued)

OTHER PUBLICATIONS

International Search Report for International Application No. PCT/AU2019/050711; International Filing date Jul. 5, 2019; Report Mail Date Sep. 13, 2019; 8 pages.
(Continued)

*Primary Examiner* — James M Kish
*Assistant Examiner* — James Moss
(74) *Attorney, Agent, or Firm* — CANTOR COLBURN LLP

(57) ABSTRACT

An ankle cuff for managing incontinence in a patient, comprising: a body; a first micro-needle electrode array located on an inner face of the body; a second micro-needle electrode array separately located from the first micro-needle electrode array; a pulse generator electrically coupled to the first and second micro-needle electrode arrays; in use, the body is configured to be worn around an ankle of the patient such that individual micro-needles of the first and second micro-needle electrode arrays insert into an epidermis of the patient; and a controller, wherein the controller controls the pulse generator to pulse the first and second micro-needle electrode arrays to electrically stimulate the posterior tibial nerve for managing incontinence in the patient.

13 Claims, 9 Drawing Sheets

(52) U.S. Cl.
CPC ..... *A61N 1/36031* (2017.08); *A61N 1/36034* (2017.08); *A61M 37/0015* (2013.01); *A61N 1/36021* (2013.01)

(56) References Cited

U.S. PATENT DOCUMENTS

| | | | |
|---|---|---|---|
| 2011/0301670 A1* | 12/2011 | Gross | A61N 1/36171 607/2 |
| 2012/0302821 A1* | 11/2012 | Burnett | A61N 1/36021 600/13 |
| 2014/0303682 A1* | 10/2014 | Siff | A61N 1/0456 607/46 |
| 2015/0335881 A1* | 11/2015 | Jenks | A61N 1/0502 607/149 |
| 2016/0303363 A1* | 10/2016 | Girouard | A61N 1/36003 |
| 2017/0361093 A1* | 12/2017 | Yoo | A61N 1/36007 |
| 2018/0296834 A1* | 10/2018 | John | A61N 1/36007 |

FOREIGN PATENT DOCUMENTS

| | | | |
|---|---|---|---|
| WO | 2016069687 | A2 | 5/2016 |
| WO | 2017132067 | A2 | 8/2017 |

OTHER PUBLICATIONS

Written Opinion for International Application No. PCT/AU2019/050711; International Filing date Jul. 5, 2019; Report Mail Date Sep. 13, 2019; 8 pages.

\* cited by examiner

ANKLE CUFF FOR MANAGING INCONTINENCE

CROSS REFERENCE TO RELATED APPLICATIONS

This application is a National Stage application of PCT/AU2019/050711, filed Jul. 5, 2019, which claims the benefit of Australian Application No. 2018902463, filed Jul. 6, 2018, both of which are incorporated by reference in their entirety herein.

FIELD OF INVENTION

The present invention relates to an ankle cuff (and corresponding method of use) capable of producing a therapeutic effect for inhibiting and/or treating various urological conditions and gastrointestinal disorders. More particularly, but by no means exclusively, the present invention relates to an ankle cuff for managing incontinence in a patient.

BACKGROUND OF INVENTION

Incontinence is considered as any involuntary loss of urine (urinary incontinence) or faeces (faecal or bowel incontinence). There are varying levels of incontinence that may be experienced by a person, from minor leaks to complete loss of control of the bladder or bowel.

Approximately 1 in 20 people suffer faecal incontinence, which can include the passing of both stool or wind involuntarily due to a lack of control. There are many causes of faecal incontinence, including the weakening of back passage muscles after having children, due to surgery, or as the result of aging.

Both urinary and faecal incontinence are more prevalent in the aging population. Some contributing factors include the weakening of muscles in the body, as well as the increased incidence of dementia that may result in a sufferer finding it difficult recognise that they need to relieve themselves.

Incontinence can be partially managed through lifestyle changes, such as performing physical activities that operate to engage and strengthen the pelvic floor. However, such activities, even when performed diligently, may only slightly improve the condition. Further, sufferers may find it difficult to perform such activities, for example, due to an aging physical frame.

Another option for sufferers of incontinence is to use continence products or aids, such as pads, condom drainages and speciality bed sheets. While providing a slightly improved quality of life to certain sufferers, such continence products do not treat the disorder and are therefore not a desirable long-term option.

Recently, developments have been made in tibial nerve neuromodulation to treat pelvic floor and gastrointestinal disorders. The tibial nerve is a branch of the sciatic nerve and passes alongside the tibia into the foot. Stimulation of the tibial nerve has been found to block signals from the brain that can trigger incontinence, as well as to strengthen muscles to aid in preventing further episodes of incontinence.

As the tibial nerve is located relatively near the surface of the skin, stimulation of the tibial nerve can be achieved by using a transcutaneous electrical nerve stimulation (TENS) machine. TENS machines are comprised of a set of bi-polar hydrogel electrode pads connected to a pulse generator. The bi-polar hydrogel electrode pads are placed on the skin with the negative electrode positioned directly above the tibial nerve and the positive electrode positioned within proximity of the negative electrode. The pulse generator then delivers an electrical pulse to the tibial nerve via the electrodes.

To aid the electrical signal reaching the tibial nerve, the anatomical location where the electrode pads are placed is often shaved, and hydrogel is applied to both the skin and the bottom of each of electrode pad. Once the electrode pads are suitably positioned, tape is used to secure them to the skin (commonly transcutaneous electrodes are hydrogel based with a sticky surface that sticks to the surface of the skin), thereby preventing movement and the potential for unwanted surrounding nerve stimulation. This preparation is not only time consuming, but also requires periodic re-application due to tape degradation and hydrogel evaporation.

Further, the frequency applied by a TENS machine is typically limited to 50 Hz, as using higher frequencies may result in the unwanted stimulation of other surrounding nerves. However, a downside to using such lower frequencies is that the patient may experience paraesthesia around the location of the electrode pads. This can cause discomfort to the patient.

An alternative to transcutaneous electrical nerve stimulation is percutaneous tibial nerve stimulation. Percutaneous stimulation involves inserting a slim needle electrode through the skin which targets the tibial nerve. Due to the targeted nature of percutaneous tibial nerve stimulation, a higher frequency pulse can be applied to the tibial nerve, thus reducing the likelihood of a patient experiencing paraesthesia during treatment.

Typically, a doctor or trained medical professional is required to precisely insert the needle electrode below the epidermis, near the medial malleolus of a patient. A second electrode is then positioned above the epidermis. Due to the procedure needing to be performed by a trained medical professional, this form of treatment is relatively costly. Further, due to the procedure being invasive, it can be painful and may result in inflammation and blood loss (which can in turn leave the patient susceptible to bacterial infections).

Another disadvantage with percutaneous tibial nerve stimulation is that the patient must remain still, typically with their leg elevated, to ensure there are no unnecessary complications (eg., falling over if the foot muscles are caused to flex during pulsing). As such, while this method may effectively strengthen a patient's muscles for treatment of incontinence, it is not suitable for everyday use in blocking signals that can result in sudden incontinence.

It would be advantageous if there was a device that provided electrical tibial nerve stimulation which ameliorated at least one of the disadvantages of current devices as outlined above.

SUMMARY OF INVENTION

In accordance with a first aspect of the present invention there is provided an ankle cuff for managing incontinence in a patient, comprising: a body; a first micro-needle electrode array located on an inner face of the body; a second micro-needle electrode array separately located from the first micro-needle electrode array; a pulse generator electrically coupled to the first and second micro-needle electrode arrays; in use, the body is configured to be worn around an ankle of the patient such that individual micro-needles of the first and second micro-needle electrode arrays insert into an epidermis of the patient; and a controller, wherein the controller controls the pulse generator to pulse the first and second micro-needle electrode arrays to electrically stimulate the posterior tibial nerve for managing incontinence in the patient.

In an embodiment the first micro-needle electrode array is a negative electrode array that locates directly superior to the posterior tibial nerve and between a medial malleolus and an Achilles tendon of the patient.

In an embodiment the second micro-needle electrode array is a positive electrode array that locates between a lateral malleolus and the Achilles tendon.

In an embodiment the second micro-needle electrode array is located directly superior to a sural nerve of the patient.

In an embodiment the first and second micro-needle electrode arrays each comprise a plurality of individual needles that have a depth of less than 1 mm and which are configured to pierce a stratum corneum layer of the epidermis.

In an embodiment the controller can program the plurality of individual needles of the first and second micro-needle electrode arrays to pulse at different amplitudes or frequencies determined by the controller.

In an embodiment the controller can program the plurality of individual needles to be grouped into two or more electrode zones that are adapted to pulse at different amplitudes or frequencies determined by the controller.

In an embodiment the first micro-needle electrode array and second micro-needle electrode array are detachable from the ankle cuff.

In accordance with a second aspect of the present invention there is provided an ankle cuff for managing incontinence in a patient, comprising: a body; a first transcutaneous negative electrode located on an inner face of the body; a second transcutaneous positive electrode separately located from the first electrode; a pulse generator electrically coupled to the first and second transcutaneous electrodes; a controller, wherein the controller controls the pulse generator to pulse the first and second transcutaneous electrodes to electrically stimulate the posterior tibial nerve for managing incontinence in the patient; and wherein the first and second transcutaneous electrodes are selected from: hydrogel electrodes, silver electrodes, platinum electrodes or metal electrodes.

In an embodiment the first transcutaneous negative electrode and second transcutaneous positive electrode are detachable from the ankle cuff.

In an embodiment of any of the aspects of the present invention the pulse is of sufficient amplitude and frequency to at least partially relieve a symptom selected from: urgent urination, urinary retention, urge incontinence, frequent urination, mixed urinary incontinence, nocturia, interstitial cystitis, bladder discomfort, pelvic pain, faecal incontinence, constipation, irritable bowel syndrome, nocturnal enuresis, erectile dysfunction and persistent pelvic pain.

In an embodiment further comprising an accelerometer and wherein, in use, the controller is configured to collect acceleration data output by the accelerometer.

In an embodiment the acceleration data is evaluated by the controller to determine at least one of a desirable time, amplitude and frequency to electrically stimulate the posterior tibial nerve and manage incontinence in the patient.

In an embodiment the controller is configured to evaluate acceleration data captured during a sleep time of the patient to determine potential nocturia events and wherein the determined nocturia events are recorded and classified as such.

In an embodiment the classified potential nocturia events are evaluated over time to predict future nocturia events for the patient and wherein the controller controls or suggests to the patient controlling the pulse generator prior to the predicted respective future periods.

In an embodiment the controller is configured to control the pulse generator to pulse at a higher amplitude for a predetermined period before the predicted future nocturia events.

In an embodiment the predetermined period is between 1 and 40 minutes before the predicted the future nocturia events.

In an embodiment when the controller determines that the patient is moving based on the collected accelerometer data, the controller is configured to control the pulse generator to pulse the electrodes at a lower amplitude than if the patient were stationary.

In an embodiment the controller determines that the patient is stationary when an acceleration of the patient is between 0.0 m/s-2.0 m/s, otherwise the patient is determined to be moving.

In an embodiment further comprising a gyroscope that is configured to output positional data of the patient and wherein the controller evaluates the positional data to determine whether the patient is standing, sitting or lying down.

In an embodiment the controller controls at least one of an amplitude and frequency of the pulse based on the positional data.

In an embodiment the pulse frequency is between 1 Hz to 100 kHz.

In an embodiment the pulse amplitude is between 0.1 m Amps to 12.0 m Amps.

In accordance with a further aspect of the present invention there is provided a method of stimulating a posterior tibial nerve of a patient, comprising; identifying a medial malleolus of the patient; placing a wearable ankle cuff on the patient such that the medial malleolus locates within a predetermined medial malleolus location of the wearable ankle cuff; pulsing a pair of electrodes located on an inner face of the wearable ankle cuff so as to stimulate the tibial nerve for managing incontinence in the patient.

In an embodiment the pair of electrodes are micro-needle electrode arrays.

In an embodiment a first of the pair of electrodes is a negative micro-needle electrode array that locates directly superior to the posterior tibial nerve and between a medial malleolus and an Achilles tendon of the patient.

In an embodiment a second of the pair of electrodes is a positive micro-needle electrode array that locates directly superficial or superior to a sural nerve of the patient and between a lateral malleolus and the Achilles tendon.

In accordance with a further aspect of the present invention there is provided a removeable insert for an ankle cuff, comprising: a first transcutaneous electrode; a second transcutaneous electrode; and a region adapted to couple to the ankle cuff such that the first and second electrode can receive a pulse from a pulse generator of the ankle cuff.

BRIEF DESCRIPTION OF DRAWINGS

Embodiments of the present invention will now be described, by way of example only, with reference to the accompanying drawings, in which.

DETAILED DESCRIPTION

Embodiments of the invention described herein relate to an ankle cuff configured to stimulate a patient's posterior tibial nerve for managing urological and gastrointestinal conditions without unwanted sensory and/or motor side effects. Management may include inhibiting, suppressing, down regulating, blocking, preventing or otherwise neuromodulating the activity of the affected neural population.

The ankle cuff may be used, for example, for managing overactive bladder systems including urgency, incontinence and frequency, mixed urinary incontinence, interstitial cystitis, urinary retention and persistent pelvic pain. Gastrointestinal disorders that can be managed by an ankle cuff as described herein, including faecal incontinence, constipation and irritable bowel syndrome.

In general terms, an ankle cuff as described herein comprises a body configured to be worn around the ankle of a patient. A first and second electrode array are each located on an inner face of the body and positioned to accurately target the patient's posterior tibial nerve. A cuff controller controls a pulse generator that is electrically coupled to the first and second electrode arrays for pulsing the electrodes (across a variable range of frequencies and wavelengths) to electrically stimulate the targeted tibial nerve for managing the condition.

Ankle Cuff Configuration

Figure 1:
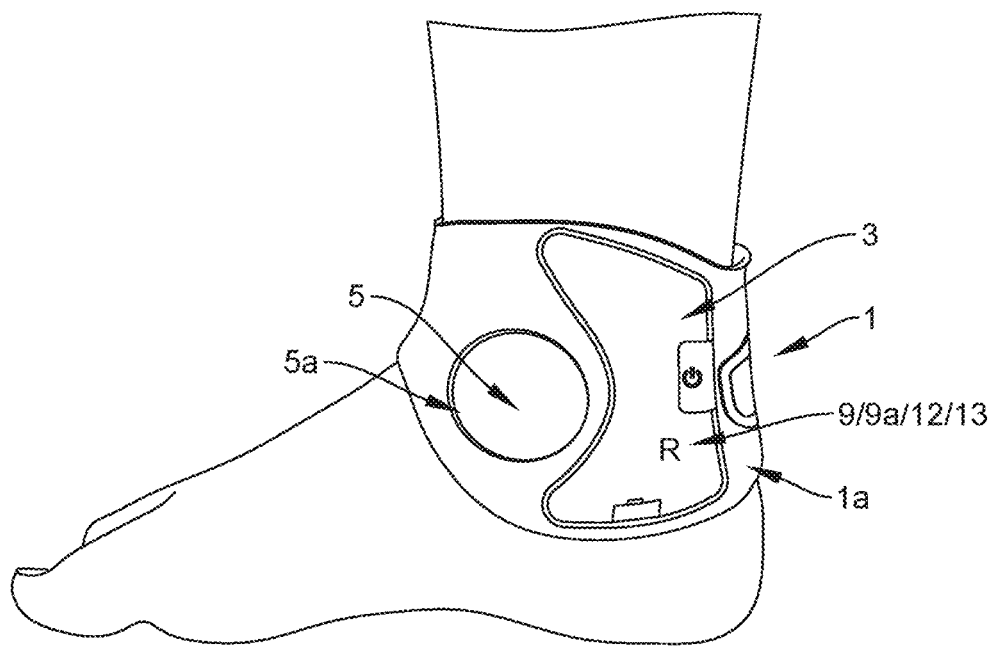
FIG. 1 is a medial side view of an ankle cuff worn by a patient, in accordance with an embodiment of the present invention.
Figure 2:
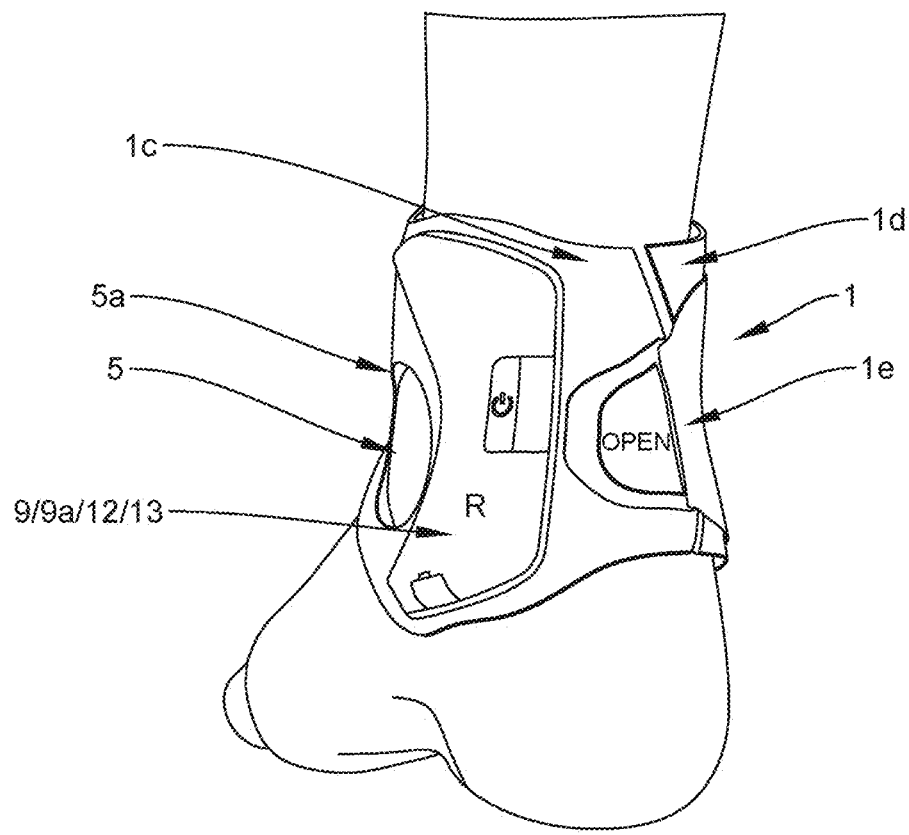
FIG. 2 is an end view of the ankle cuff shown in FIG. 1 worn by the patient.
Figure 3:
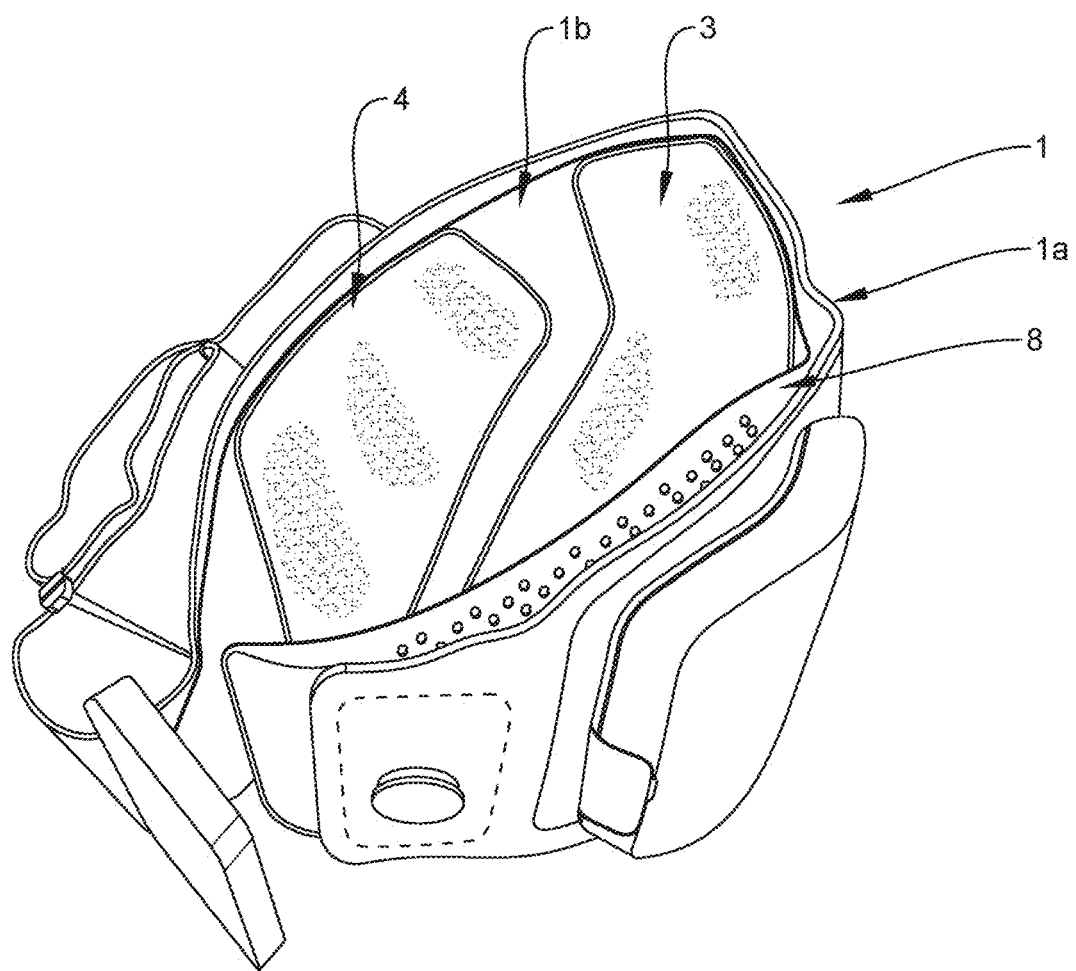
FIG. 3 is a perspective view of the ankle cuff of FIG. 1 (removed from the patient) illustrating internally disposed electrode arrays.

With reference to FIGS. 1 to 3 there is shown an ankle cuff in accordance with a first embodiment of the invention. The ankle cuff (1) comprises a body (1a) configured to be worn around an ankle of a patient. The electrode arrays take the form of micro-needle arrays. A negative micro-needle electrode array (3) is located on an inner face (1b) of the body (1a) superior to at least a portion of the patient's posterior tibial nerve (2). A positive micro-needle electrode array (4) is also located on the inner face of the cuff body (1a) separate from the first micro-needle electrode array (3).

Each micro-needle electrode array (3, 4) comprises of a plurality of individual needles that, according to the illustrated embodiment, are less than or equal to 1 mm long. The individual needles are closely spaced such that the large electric fields needed for electroporation can be achieved at relatively low voltages. In addition, placing the micro-needle arrays (3, 4) in the illustrated locations results in low interface impedance while allowing for a highly localised pulse for effective stimulation of the posterior tibial. These factors allow the tibial nerve (2) to be stimulated at a relatively low amplitude, in turn allowing for longer battery life (i.e. for powering the pulse generator, as will be described in more detail in subsequent paragraphs).

When worn as shown in FIGS. 1 and 2, the micro-needle electrode arrays (3, 4) are applied to the patient's skin at a low compression force, piercing only the stratum corneum layer. This is painless for the patient as no pain receptors are triggered, nor is any blood drawn. This minimises patient discomfort and risk of infection after removal of the cuff (1).

Further, since the micro-needle arrays (3, 4) are dry electrodes they do not require any form of moisture (i.e. hydrogel, water, etc) to provide an effective pulse and can therefore be applied to the skin without the need for any specific preparation or additional equipment.

The body (1a) is configured to open for receiving the patient's ankle and close for securing around the patient's ankle. With specific reference to FIG. 2, the body (1a) is formed of two hinged parts (1c. 1d) that releasably couple at a non-hinged end for opening and closing around a patient's ankle. According to the illustrated embodiment, the non-hinged end is located adjacent the patient's Achilles tendon (6). As shown, a clasp 1(e) is provided for releasably coupling the two parts (1c, 1d) at the non-hinged end (though it will be understood that any suitable means could be used for releasably coupling the two parts).

In an alternative embodiment, the body (1a) may take the form of a single length of strap that is configured to wrap around the patient's ankle, with the ends being secured by way of a magnets, clip, buckle, Velcro™, zipper, or other suitable securing means.

The body (1a) is advantageously configured such that the negative micro-needle electrode array (3) always locates directly superior to the posterior tibial nerve (2), as will now be described with additional reference to FIG. 4.

Figure 4:
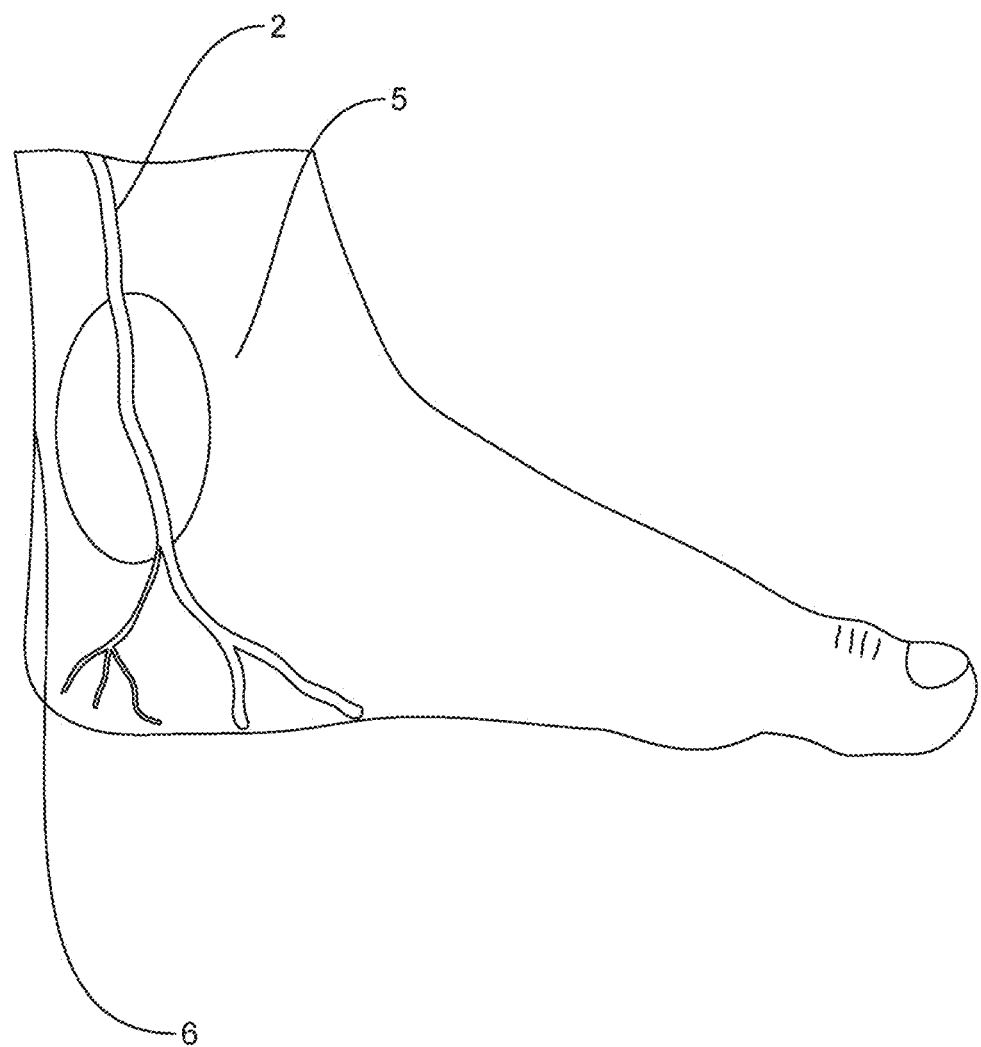
FIG. 4 is a medial side view of a patient's ankle illustrating anatomical land marks for positioning the ankle cuff of FIG. 1.

As shown in FIG. 4, the tibial nerve (2) is located between a medial malleolus (5) and an Achilles tendon (6) of the patient. The medial malleolus (5) is a bony protrusion on the inner ankle. The cuff (1) uses at least one of these two anatomical land marks for positioning so that it can consistently locate the negative array (3) directly above the posterior tibial nerve (2). According to the illustrated embodiment, the body (1a) of the cuff (1) comprises a medial aperture (5a) that is sized and shaped to receive the medial malleolus (5). The negative micro-needle electrode array (3) is disposed on the inner face 1b between the aperture (5a) and the clasped end. In use, the cuff (1) is located over the patient's ankle such that the medial aperture (5a) surrounds the medial malleolus (5) and sits generally flush about the surrounding skin (thereby exposing the medial malleolus's bony ridge). This is best shown in FIGS. 1 and 2.

Figure 5:
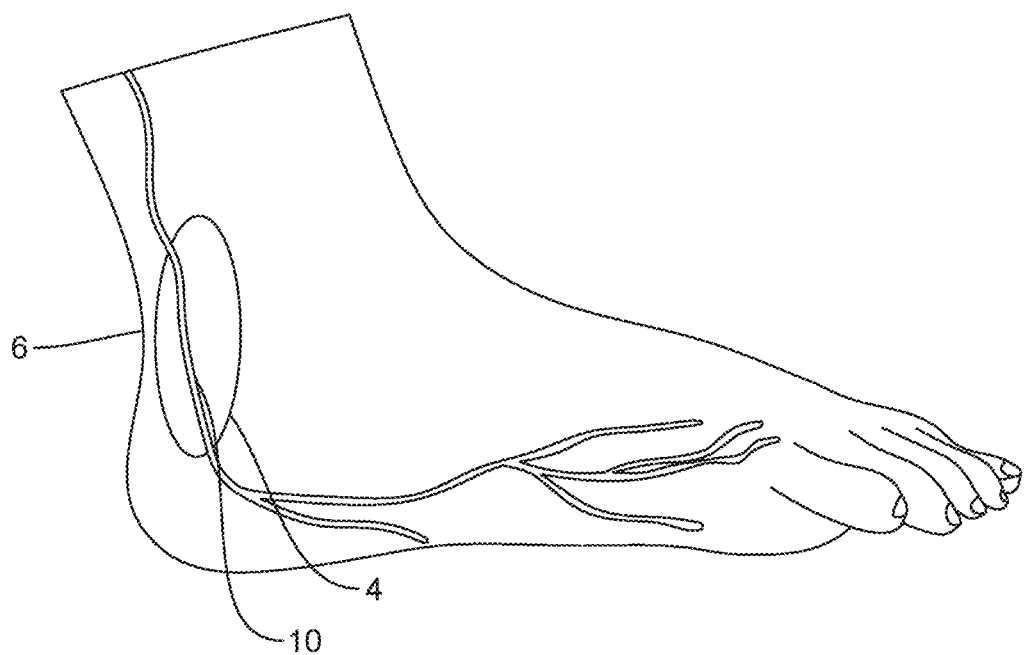
FIG. 5 is a lateral side view of a patient's ankle illustrating anatomical land marks for positioning the ankle cuff of FIG. 1.
Figure 6:
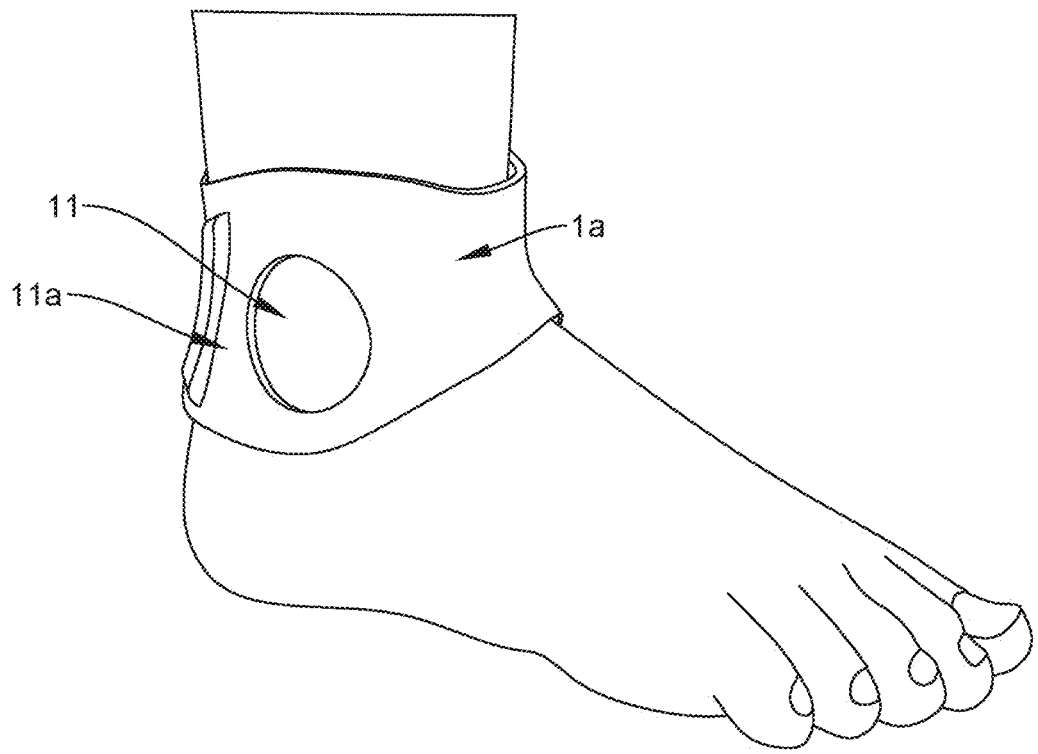
FIG. 6 is a lateral side view of the ankle cuff of FIG. 1, in accordance with an embodiment of the present invention.

The positive micro-needle electrode array (4) may be located in any suitable location on the inner wall (1b) of the body (1a) separate from the negative electrode array (3). However, according to the illustrated embodiment, the positive array (4) is located directly superior to the sural nerve (see FIG. 5 sans cuff (1) for ease of reference). This configuration has the benefit of additionally stimulating the sural nerve (10) which has been found to reduce the potential for paraesthesia.

To ensure correct positioning of the positive array (4), and for general patient comfort, a lateral aperture (11b) in the cuff body (1a) is configured to locate over the lateral malleolus (11) in the same manner as for the medial aperture (5a). It will be understood that the cuff (1) may incorporate only a medial or lateral aperture, however, while still allowing for accurate positioning of the electrode arrays (3, 4).

The ankle cuff (1) further comprises a controller (9) adapted to control a pulse generator (9a) for pulsing the micro-needle electrode arrays (3, 4). The controller (9) and pulse generator (9a) are powered by an integrated battery.

The controller (9) may, for example, comprise a microcontroller having a wireless transceiver for receiving patient commands from a remote device. For example, the controller (9) may comprise a wireless transceiver (e.g. Bluetooth) for communicating with a mobile phone or other suitable electronic device having an input device (e.g. keyboard, touch screen interface, etc.) and loaded with software capable of communicating with the controller (9)). In an alternative embodiment, the controller (9) may be communicable with one or more controls located on the ankle cuff (1) for receiving patient commands. For example, a "pulse" button may be provided on the ankle cuff (1) which causes the controller (9) to instruct the pulse generator (9a) to pulse the electrode arrays (3, 4).

The pulse applied by the pulse generator (9a) is of sufficient amplitude and frequency to at least partially relieve a symptom selected from: urgent urination, urinary retention, urge incontinence, frequent urination, mixed urinary incontinence, nocturia, interstitial cystitis, bladder discomfort, pelvic pain, faecal incontinence, constipation, irritable bowel syndrome, nocturnal enuresis, erectile dysfunction and persistent pelvic pain.

Once the cuff (1) has been suitably located and secured, the patient can carry out a basic test to confirm that the electrode arrays (3, 4) are located in the correct position. In one embodiment, correct positioning is determined by noting a motor response when the pulse amplitude is increased to create halux reaction (plantar flexion of great toe or fanning of all toes), or where the patient notes a tingling sensation, pulsing, or movement in the great toe.

The amplitude, frequency and wavelength of pulse (hereafter "pulse parameters") necessary to stimulate the tibial nerve may vary from patient to patient. By way of example, some pulse parameter settings are shown below in Table 1.

TABLE 1

| Patient | Amplitude (mA) | Frequency (Hz) | Wavelength (ms) |
| --- | --- | --- | --- |
| Male 70 yrs | 2.5 | 10 | 200 |
| Female 68 yrs | 1.2 | 33 | 210 |
| Female 62 yrs | 3.8 | 24 | 300 |
| Female 50 yrs | 8.0 | 60 | 210 |
| Male 56 yrs | 4.5 | 100 | 200 |

Figure 7A:
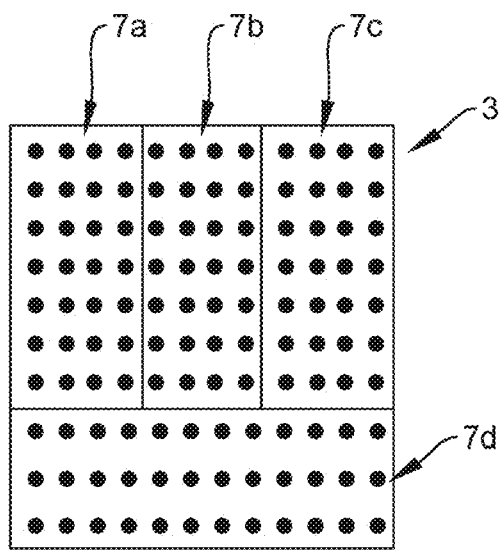
FIGS. 7a, 7b and 7c are schematics showing electrode arrays partitioned into multiple zones, in accordance with an embodiment of the present invention
Figure 7B:
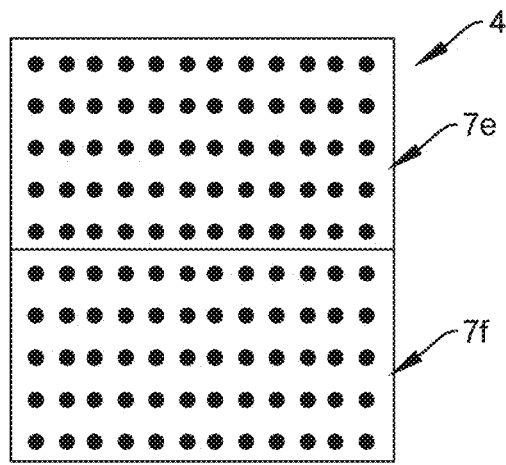
Figure 7C:
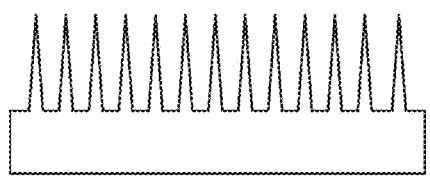

Depending on the desired implementation, the micro-needle electrode arrays (3, 4) may be split into one or more zones (7) of individual electrodes, as schematically illustrated in FIGS. 7a, 7b and 7c. The zones (7) may be predefined by the controller (9) or manually determined by the patient (via their electronic input device). According to the illustrated embodiment depicted in FIGS. 7a and 7b, the negative micro-needle electrode array (3) is split into four predefined zones (7a, 7b, 7c, 7d), while the positive micro-needle electrode array (4) is split into two predefined zones (7e, 7f). Persons skilled in the art will appreciate that the zones (7) may be the same or different sizes and that each array can include any number of zones (7). FIG. 7c is a side view illustrating the needles of the positive and negative micro-needle electrode arrays (3, 4).

A patient may select a number of parameters for each zone (7), including, but not limited to, the pulse parameters for each zone (7), as well as whether the zones (7) are to be "on" (pulsed) or "of" (not pulsed) during a pulsing session. The patient may instruct the controller (9) to select zone parameters based on personal preference. For instance, through trial and error the patient may determine that when an upper two zones of the negative micro-needle electrode array (3) are in an "off" state they experience less paraesthesia.

Persons skilled in the art will also appreciate that either uniformed and un-uniformed electrical stimulation can be directed towards the posterior tibial nerve (2) by way of the arrays (3, 4). Un-uniformed stimulation may require less battery power to be used for generating sufficient amplitude directed towards the posterior tibial nerve (2). Further, by being able to tailor individual amplitudes for each needle on the surface of the micro-needle electrode array, the ankle cuff (1) may be able to deliver targeted stimulation towards the patient's posterior tibial nerve (2). For example, the micro-needles closest to the posterior tibial nerve (2) may be configured to have a greater amplitude than those further away. This can also minimise unwanted paraesthesia side effects at the electrodes furthest away from the posterior tibial nerve (2).

Figure 8:
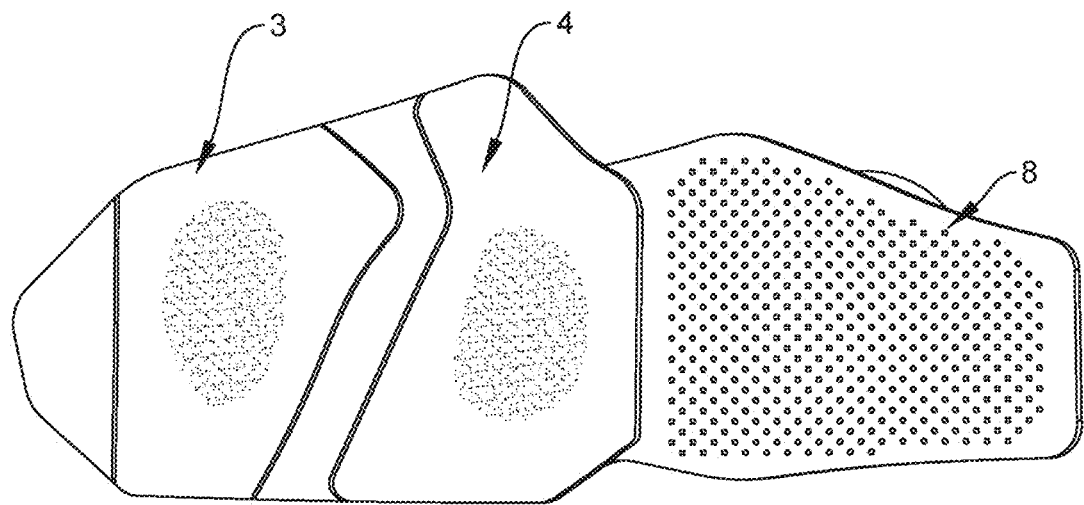
FIG. 8 is a schematic showing a removable insert for the cuff of FIG. 1, in accordance with an embodiment of the invention.
Figure 9A:
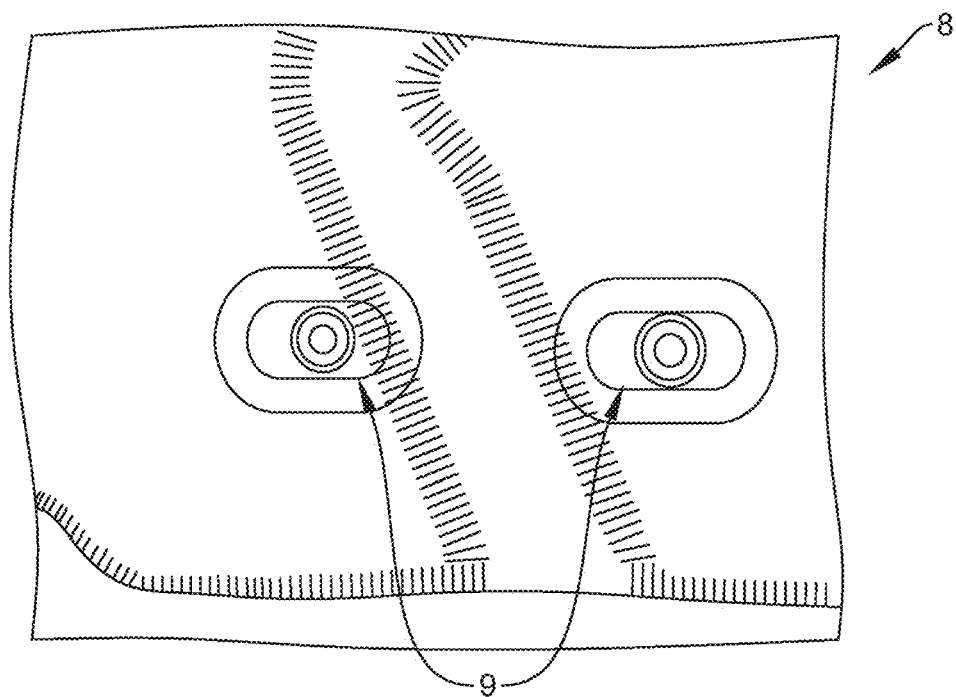
FIGS. 9a and 9b are schematics illustrating the cap and socket of the snap fasteners in accordance with an embodiment of the present invention.
Figure 9B:
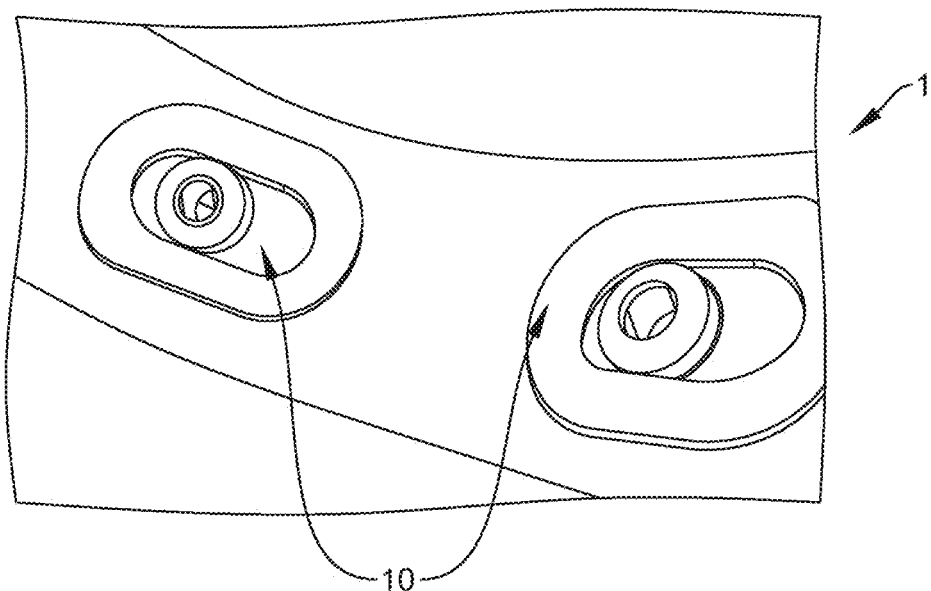

With reference to FIG. 8, there is shown a removable insert (8) for the cuff (1). The electrode arrays (3, 4) are disposed on or within the insert (8), allowing them to be replaced without the need to replace the entire ankle cuff (1). The removable insert (8) may be attached to the inner wall (1b) of the cuff (1) via a fastening means such as Velcro™, snap lock clips, adhesive, or other suitable fastening means. According to the illustrated embodiment, the removable insert (8) is formed of a soft fabric material. An electrical connection between the arrays (3, 4) and the pulse generator (9a) may be made by way of conductive snap fasteners (9) illustrated in FIGS. 9a and 9b. The snap fasteners (9) are comprised of a cap (9a) disposed on the insert (8) and a socket (9b) disposed on the inner wall (1b) of the cuff (1).

In an alternative embodiment to that shown in FIGS. 1 to 8, the ankle cuff may comprise non-micro needle electrode arrays, including transcutaneous electrodes such as hydrogel electrodes, silver electrodes, platinum electrodes or metal electrodes. Further, the ankle cuff may comprise a combination of transcutaneous electrodes and percutaneous electrodes such as electrodes comprised of a hydrogel base with micro needle electrode arrays embedded onto the hydrogel base.

Ankle Cuff Pulse Frequency and Amplitude

Persons skilled in the art will appreciate that paraesthesia effects, if any, can vary between patients. As such, two patients receiving the same pulse may experience varying degrees of paraesthesia. To comfortably receive treatment, a patient may to modify one or more of the pulse parameters to minimise or obviate any paraesthesia effects.

In an embodiment of the invention, a sub-threshold amplitude and motor activation amplitude may be determined either automatically or by the patient. The sub-threshold amplitude may be an amplitude where the tibial nerve is stimulated, but no paraesthesia or planar foot flexion is experienced. The motor activated amplitude activates a motor response such as paraesthesia of planar foot flexion. These values may be the same or different in the supine (horizontal) position, Fowler's partition (when sitting) and a standing position (vertical). In an embodiment, the controller (9) may be programmed to consistently stimulate the posterior nerve (2) at the sub-threshold amplitude for strengthening the patient's muscles.

Persons skilled in the art will appreciate the sub-threshold amplitude and motor activation amplitude will vary dependant on a number of factors including but not limited to; patient physiology, xeroderma (dry skin), electrical impedance, position of electrodes, position of nerves, body position, etc.

In an embodiment of the invention wherein the ankle cuff is adapted with micro-needle electrode arrays, high frequency pulse modulation of between 3 khz to 100 khz is desirable to significantly reduce paraesthesia side effects and neural motor activation. These high frequencies can be applied by the controller (9) in a cycling mode, such that the pulse is applied for between 1 m/s-2 m/s and then stopped for 1 m/s-1 m/s.

The pulse amplitude is desirably set between 0.1 m Amps to 12.0 m Amps. To determine the specific desired amplitude for a patient, the pulse generator (9a) may controlled to send pulses at increasing amplitude until a neural motor response is activated, or until paraesthesia is felt in the area surrounding the electrodes.

In an embodiment of the invention the controller (9) is programmed to monitor electrical impendence levels between the skin and the electrode arrays (3, 4) and automatically adjust amplitude levels (i.e. based on the resulting levels) to reduce the risk of overstimulation resulting in severe burns and pain. For example, if only a small area of the micro-needle electrode array is providing a pulse with the desired current (e.g. due to electrode peeling), the controller (9) will decrease or even cease the pulse to prevent burn and discomfort.

Ankle Cuff with Accelerometer

In an embodiment of the invention, the ankle cuff (1) further comprises an accelerometer (12). The accelerometer (12) may be positioned on the cuff (1) in any suitable location. In use, the controller (9) is configured to collect data output by the accelerometer (hereafter "acceleration data") when the ankle cuff (1) is worn by the patient.

The acceleration data may be evaluated by the controller (9) to determine at least one of a desirable time, amplitude and frequency to electrically stimulate the posterior tibial nerve for managing incontinence in the patient.

In one embodiment, the controller (9) is programmed to evaluate acceleration data captured while the patient is sleeping to determine and record potential nocturia events. In one embodiment the patient tells the controller (9) when sleep time is to commence (e.g. using their input device). Alternatively, the controller (9) may automatically make this determination based on an evaluation of the acceleration data and current time. For example, the controller (9) may be programmed to recognised that the patient is asleep when they have remained still for more than 10 minutes after 9 pm at night.

In one embodiment, the controller (9) is programmed to register a potential nocturnal event when the patient moves during the night for more than a predefined period. In an embodiment, the patient may subsequently validate this registration using their input device. The acceleration data may be evaluated over time to predict future nocturia events. For example, acceleration data collected over a three-day period may indicate that a patient consistently experiences a nocturia event at 11 pm and 3 am every night. As such, a prediction is made that future nocturia events will occur at 11 pm and 3 am subsequent nights. The controller (9) can then acutely stimulate the posterior tibial nerve (2) before the predicted nocturia event with the aim of preventing those events from happening. The stimulation may occur anywhere between 1 second and 2 hours before the predicted future nocturia event, depending on the patient.

In the event the patient has previously selected that the posterior tibial nerve be consistently stimulated at a sub-threshold range, the controller (9) will instruct the pulse generator (9a) to pulse at a higher amplitude before the predicted future nocturia event. Persons skilled in the art will appreciate that the acceleration data could be collected over any number of days for determining nocturia event trends.

Clinically, studies have proved that movement can minimise or even eliminate urinary urgency. In use, the controller (9) can be programmed to continuously collect acceleration data to determine when the patient is accelerating so that the pulsing can either be ceased, or the pulse amplitude decreased during this time. Ceasing or decreasing the amplitude may also minimise any discomfort and unwanted motor activation that can inhibit the patient while walking or running.

Ankle Cuff with Gyroscope

In an embodiment of the invention, the ankle cuff (1) further comprises a gyroscope (13). The gyroscope (13) is configured to output positional data of the patient by measuring orientation and angular velocity of the cuff (1).

The controller (9) is adapted to evaluate the positional data to determine whether the patient is standing, sitting or lying down. Based on the orientation of the patient, one or more pulse parameters may be adjusted. For example:

| Patient (1) - Male 65 years old | | | |
|---|---|---|---|
| Orientation | Frequency | Wave length | Amplitude |
| Sitting | 33 Hz | 210 ms | 2.5 mA |
| Standing | 33 Hz | 210 ms | 3.0 mA |
| Laying down | 33 Hz | 210 ms | 2.0 mA |

| Patient (2) - Female 42 years old | | | |
|---|---|---|---|
| Orientation | Frequency | Wave length | Amplitude |
| Sitting | 33 Hz | 210 ms | 4.5 mA |
| Standing | 35 Hz | 210 ms | 5.0 mA |
| Laying down | 35 Hz | 400 ms | 2.0 mA |

| Patient (3) - Female 86 years old | | | |
|---|---|---|---|
| Orientation | Frequency | Wave length | Amplitude |
| Sitting | 60 Hz | 300 ms | 5.0 mA |
| Standing | 33 Hz | 210 ms | 3.0 mA |
| Laying down | 33 Hz | 410 ms | 1.0 mA |

A person skilled in the art would appreciate that, since the nerve to electrode association is likely to be altered at each orientation, it is more likely that the controller will adjust the amplitude to achieve the desired outcome and keep the frequency settings unchanged.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The preceding description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In addition, the foregoing describes only some embodiments of the inventions, and alterations, modifications, additions and/or changes can be made thereto without departing from the scope and spirit of the disclosed embodiments, the embodiments being illustrative and not restrictive.

Furthermore, the inventions have described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the inventions. Also, the various embodiments described above may be implemented in conjunction with other embodiments, e.g., aspects of one embodiment may be combined with aspects of another embodiment to realize yet other embodiments.

Further, each independent feature or component of any given assembly may constitute an additional embodiment.

The invention claimed is:

1. An ankle cuff for managing incontinence in a patient comprising:
   a body;
   a first negative micro-needle electrode array located on an inner face of the body directly superior to the posterior tibial nerve and between the medial malleous and Achilles tendon of the patient; the body configured to have at least one aperture sized and shaped to receive the corresponding medial and/or lateral malleolus of the patient's ankle to position the first negative micro-needle electrode array superior to the posterior tibial nerve of the patient;
   a second micro-needle electrode array separately located from the first micro-needle electrode array;
   a pulse generator electrically coupled to the first and second micro-needle electrode arrays; the body being configured to be worn around an ankle of the patient such that individual micro-needles insert into an epidermis of the patient; and a controller, wherein the controller controls the pulse generator to pulse the first and second micro-needle electrode arrays to electrically stimulate the posterior tibial nerve;
   an accelerometer wherein, in use, the controller is configured to collect acceleration data output by the accelerometer to determine when the patient is moving and wherein when the patient is moving, the controller is configured to control the pulse generator to pulse the electrodes at a lower amplitude than if the patient were stationary;
   wherein the acceleration data is evaluated by the controller to determine at least one of a time, wavelength, amplitude and frequency to electrically stimulate the posterior tibial nerve and manage incontinence in the patient;
   wherein the controller is configured to evaluate acceleration data captured during a sleep time of the patient to determine potential nocturia events and wherein the potential nocturia events are evaluated over time to predict future nocturia events for the patient and wherein the controller activates the pulse generator prior to avert the potential nocturia events.

2. The ankle cuff of claim 1, wherein the second micro-needle electrode array is a positive electrode array that is located between a lateral malleolus or the medial malleolus and the Achilles tendon.

3. The ankle cuff of claim 1, wherein the first and second micro-needle electrode arrays each comprise a plurality of individual needles that have a depth of less than 1 mm and which are configured to pierce a stratum corneum layer of the epidermis.

4. The ankle cuff of claim 3, wherein the controller can program the plurality of individual needles of the first and second micro-needle electrode arrays to pulse at different wavelengths, amplitudes or frequencies determined by the controller.

5. The ankle cuff of claim 4, wherein the controller can program the plurality of individual needles of a micro-needle electrode array to be grouped into two or more electrode zones that are adapted to pulse at different wavelength, amplitudes or frequencies determined by the controller.

6. The ankle cuff of claim 1, wherein the first micro-needle electrode array and second micro-needle electrode array are detachable from the ankle cuff.

7. The ankle cuff of claim 1, wherein the electrical stimulation of the posterior tibial nerve relieves at least one symptom selected from: urgent urination, urinary retention, urge incontinence, frequent urination, mixed urinary incontinence, nocturia, interstitial cystitis, bladder discomfort, pelvic pain, faecal incontinence, constipation, irritable bowel syndrome, nocturnal enuresis, erectile dysfunction and persistent pelvic pain.

8. The ankle cuff of claim 1, wherein the controller is configured to control
   the pulse generator to pulse at a higher amplitude for a predetermined period before the predicted future nocturia events.

9. The ankle cuff of claim 1, wherein the predetermined period is between
   1 and 40 minutes before the predicted future nocturia events.

10. The ankle cuff of claim 1, wherein the controller determines that the patient is moving based on the collected accelerometer data and the controller is configured to control the pulse generator at a lower amplitude than if the patient were stationary.

11. The ankle cuff of claim 1, further comprising a gyroscope that is configured to output positional data of the patient and wherein the controller evaluates the positional data to determine whether the patient is standing, sitting or lying down and wherein the controller controls at least one of an amplitude, wavelength and frequency of the pulse based on the positional data.

12. The ankle cuff of claim 1, wherein the pulse frequency is between 1 Hz to 100 kHz and wherein the pulse amplitude is between 0.1 m Amps to 12.0 m Amps.

13. The ankle cuff of claim 1 wherein the first micro-needle electrode array comprises at least one percutaneous micro-needle that inserts into an epidermis of the patient's skin.

* * * * *